United States Patent
Corbeil et al.

(10) Patent No.: US 8,018,717 B2
(45) Date of Patent: Sep. 13, 2011

(54) FACILITY FOR COOLING A DETECTION DEVICE AND DETECTION DEVICE

(75) Inventors: James Corbeil, Knoxville, TN (US);
Stefan Stocker, Grossenseebach (DE)

(73) Assignee: Siemens Aktiengesellschaft, Munich (DE)

( * ) Notice: Subject to any disclaimer, the term of this patent is extended or adjusted under 35 U.S.C. 154(b) by 251 days.

(21) Appl. No.: 12/453,153

(22) Filed: Apr. 30, 2009

(65) Prior Publication Data

US 2009/0272517 A1 Nov. 5, 2009

(30) Foreign Application Priority Data

May 2, 2008 (DE) .......... 10 2008 021 898

(51) Int. Cl.
*H05K 7/20* (2006.01)
(52) U.S. Cl. ....... 361/699; 361/719; 361/721; 165/80.4; 165/104.33; 174/15.1
(58) Field of Classification Search .......... None
See application file for complete search history.

(56) References Cited

U.S. PATENT DOCUMENTS

| | | | | |
|---|---|---|---|---|
| 6,084,771 A * | 7/2000 | Ranchy et al. | ............... | 361/699 |
| 6,542,365 B2 * | 4/2003 | Inoue | ............... | 361/699 |
| 7,042,725 B2 * | 5/2006 | Martin et al. | ............... | 361/699 |
| 7,130,191 B2 * | 10/2006 | Lin et al. | ............... | 361/695 |
| 7,230,334 B2 * | 6/2007 | Andry et al. | ............... | 257/713 |
| 7,254,027 B2 * | 8/2007 | Belady et al. | ............... | 361/704 |
| 7,547,966 B2 * | 6/2009 | Funakoshi et al. | ............ | 257/707 |
| 7,710,723 B2 * | 5/2010 | Korich et al. | ............... | 361/699 |
| 7,755,897 B2 * | 7/2010 | Chen et al. | ............... | 361/707 |
| 7,764,504 B2 * | 7/2010 | Phillips et al. | ............... | 361/715 |
| 7,835,151 B2 * | 11/2010 | Olesen | ............... | 361/689 |
| 2007/0102641 A1 | 5/2007 | Schmand et al. | | |

FOREIGN PATENT DOCUMENTS

| | | |
|---|---|---|
| DE | 102006025764 A1 | 12/2007 |
| DE | 102007009184 A1 | 8/2008 |
| DE | 102007019296 A1 | 10/2008 |

* cited by examiner

*Primary Examiner* — Boris L Chervinsky
(74) *Attorney, Agent, or Firm* — Harness, Dickey & Pierce, P.L.C.

(57) ABSTRACT

A facility is disclosed for cooling a detection device. In at least one embodiment, the facility includes at least one first cooling unit, through which a thermal contact to the detection device is able to be established and through which heat arising during operation of the detection device is able to be removed; and at least one second cooling unit, which is arranged so that heat from the environment of the detection device can be discharged through it. In at least one embodiment, this has the advantage of largely shielding the first cooling unit from incident heat which allows the detection device to be efficiently cooled.

10 Claims, 2 Drawing Sheets

FACILITY FOR COOLING A DETECTION DEVICE AND DETECTION DEVICE

PRIORITY STATEMENT

The present application hereby claims priority under 35 U.S.C. §119 on German patent application number DE 10 2008 021 898.7 filed May 2, 2008, the entire contents of which is hereby incorporated herein by reference.

FIELD

At least one embodiment of the present invention generally relates to a facility for cooling a detection device and/or to a detection device.

BACKGROUND

In medical imaging so-called "hybrid modalities" are becoming increasingly important, for example PET-CT, SPECT-CT, PET-MR and SPECT-MR. The meanings of these abbreviations are as follows:
PET: Positron Emission Tomography
CT: Computer Tomography
SPECT: Single Photon Emission Computed Tomography
MR: Magnetic Resonance tomography The advantage of these combinations is the connection of a modality with a high local resolution (especially MR or CT) to a modality with high sensitivity (especially SPECT or PET). Reference is made below to a combined PET-MR system. The embodiments of present invention can however be transferred in general to all forms of hybrid modalities or to related measurement processes.

PET uses the particular characteristics of the positron emitter and positron annihilation for quantitative determination of the function of organs or cell areas. In such cases corresponding radio pharmaceuticals which are marked with radio nuclides are administered to the patient before the examination. As they decay, the radio nuclides transmit positrons which after a short distance interact with an electron, which causes so-called annihilation to occur. This produces two gamma quants which fly off in opposite directions (offset by 180°) to each other. The Gamma quants are detected by two opposing PET detector modules within a specific time window (coincidence measurement), which determines the location of the annihilation to a position on the connecting line between these two detector modules.

For verification, the detector module for the PET must generally cover a majority of the gantry arc length. It is subdivided into detector elements of a few millimeters side length. Each detector element, on detection of a Gamma quant, generates an event recording which specifies the time as well as the verification point, i.e. the corresponding detector element. This information is transmitted to high-speed logic and compared. If two events fall within a maximum time spacing, a Gamma decay process on the connecting line between the two associated detector elements is assumed. The PET image is reconstructed with a tomography algorithm, i.e. what is referred to as back projection.

Since MR systems operate with high magnetic fields, the use of compatible materials within these systems is thus required. Particular attention should be paid in the construction of the PET detectors in combined PET systems to the detectors being insensitive to magnetic fields.

US 2007/0102641 A1 describes a combined PET-MR in which lutetium oxyorthosilicate (LSO) is used as a scintillation crystal for converting the Gamma-quants into light and avalanche photo diodes (APD) are used for detection of the light. The APDs are connected to preamplifiers. A ring of such PET detectors is arranged within an MR device. This allows MR and PET data sets to be recorded simultaneously. A comparable arrangement is known from U.S. Pat. No. 7,218,112 B2.

With the frequently used semiconductor amplifiers and semiconductor detectors (Avalanche Photo diodes, APD) the amplification particularly depends on the temperature. Since the components are subjected to temperature variations during operation cooling is required. The supply of cooled air allows the temperature of the amplifiers and photo diodes to be regulated. When air at a constant temperature is used the temperature of the amplifiers is produced from the equilibrium of the generated heat and the heat emitted by the air over the surface of the amplifiers. The cooling can be implemented in the same way for other parts of the detection system.

The APDs are however not just subjected to temperature fluctuations because of their operation. In particular the proximity to the gradient coil and the excitation coil of the MR system caused by the compact design represents an external heat source acting on the APD. The temperature of a gradient coil during operation is typically between 20 and 80° C. These temperature differences also act on the APD and thereby on their amplification. The effects of this heat source can also only be overcome with difficulty using air cooling.

SUMMARY

In at least one embodiment of the present invention, an improved apparatus is provided for cooling detectors. In at least one embodiment, a corresponding improved detection device is provided.

In accordance with at least one embodiment, an apparatus for cooling a detection device is specified having least the following features:
  At least one first cooling unit, through which a thermal contact to the detection device is able to be established and through which heat arising during operation of the detection device is able to be removed and
  At least one second cooling unit, which is arranged so that heat from the surroundings of the detection device can be discharged through it.

While the first cooling unit actively operates on the heat generated in the APD itself and thereby stabilizes the amplification, the second cooling unit screens out incident heat from the environment from the detection device. The heat of the environment does not reach the detection unit which can thus be stably cooled with comparatively little effort.

In an advantageous embodiment of the invention the two cooling units are arranged above the detection device as a stack. Especially with the irradiation of components with wide temperature fluctuations, such as one or more gradient coils in MR systems, this has the advantage that both the detection device itself and also the first cooling unit will be protected against being heated by the components.

A development of the invention is advantageous in that the channels of the first and the second cooling unit are linked serially into a coolant circuit. This makes a comparatively simple implementation of the two cooling units into a single coolant circuit possible.

In an advantageous embodiment of the invention the first cooling unit and the second cooling unit are arranged in the cooling circuit such that coolant flows through the first cooling unit before the second cooling unit. This guarantees a constant temperature of the first cooling unit which is used for direct cooling of the detection device. In this way the heat produced there can be reliably discharged. The incident heat is screened out by the second cooling unit. There is thus no influence by greater temperature fluctuations from the environment on the first cooling unit.

For efficient removal of heat from the selection device, in an advantageous embodiment of the invention, the first cooling unit features a cooling surface, through which a thermal contact to the detection device is able to be established.

In a further advantageous embodiment of the invention the cooling units feature further cooling surfaces, through which electronic components of the detection device are able to be brought into thermal contact with at least one of the cooling units.

A detection device with one of the example embodiments of the invention and at least one or more detector unit also has the advantages mentioned.

One advantageous embodiment of the detection device comprises a processing unit connected electrically to the detector unit for electrical signals of the detector unit. By signal processing within the selection device the already prepared signal only needs to be passed on. This is especially of advantage in restricted space situations in the environment of the detection device.

An embodiment of the detection device is advantageous in that the processing unit comprises at least one circuit board on which electronic components are arranged and which is arranged such that each of the components is in thermal contact with one of the cooling units. In this way separate cooling units for cooling down the miscellaneous electronic components can be avoided.

In an advantageous embodiment of the detection device a number of circuit boards are provided with components which are arranged to alternate with the cooling units. This enables the maximum power of the cooling units to be exploited. For example the sequence can be such that the cooling unit is in direct thermal contact with the detector unit. Arranged on the opposite side to the cooling unit is a first circuit board, behind which the second cooling unit is arranged. Another circuit board is arranged behind the second cooling unit. Alternately it is possible for a further circuit board to be arranged between the first cooling unit of the detector unit. In each example all cooling surfaces of the cooling units are used for cooling.

A detection device is advantageous in that the boards lying above and below one of the cooling units respectively are connected by flexible intermediate sections. This allows simplified production of the boards, which can be implemented in one piece for example. The flexible intermediate sections or flexible areas of a one-piece board allow said board to simply lie around the cooling units, which greatly reduces the manufacturing effort.

BRIEF DESCRIPTION OF THE DRAWINGS

Further advantages and embodiments of the invention emerge from the example embodiments described below in conjunction with the figures. The figures are as follows.

DETAILED DESCRIPTION OF THE EXAMPLE EMBODIMENTS

Figure 1:
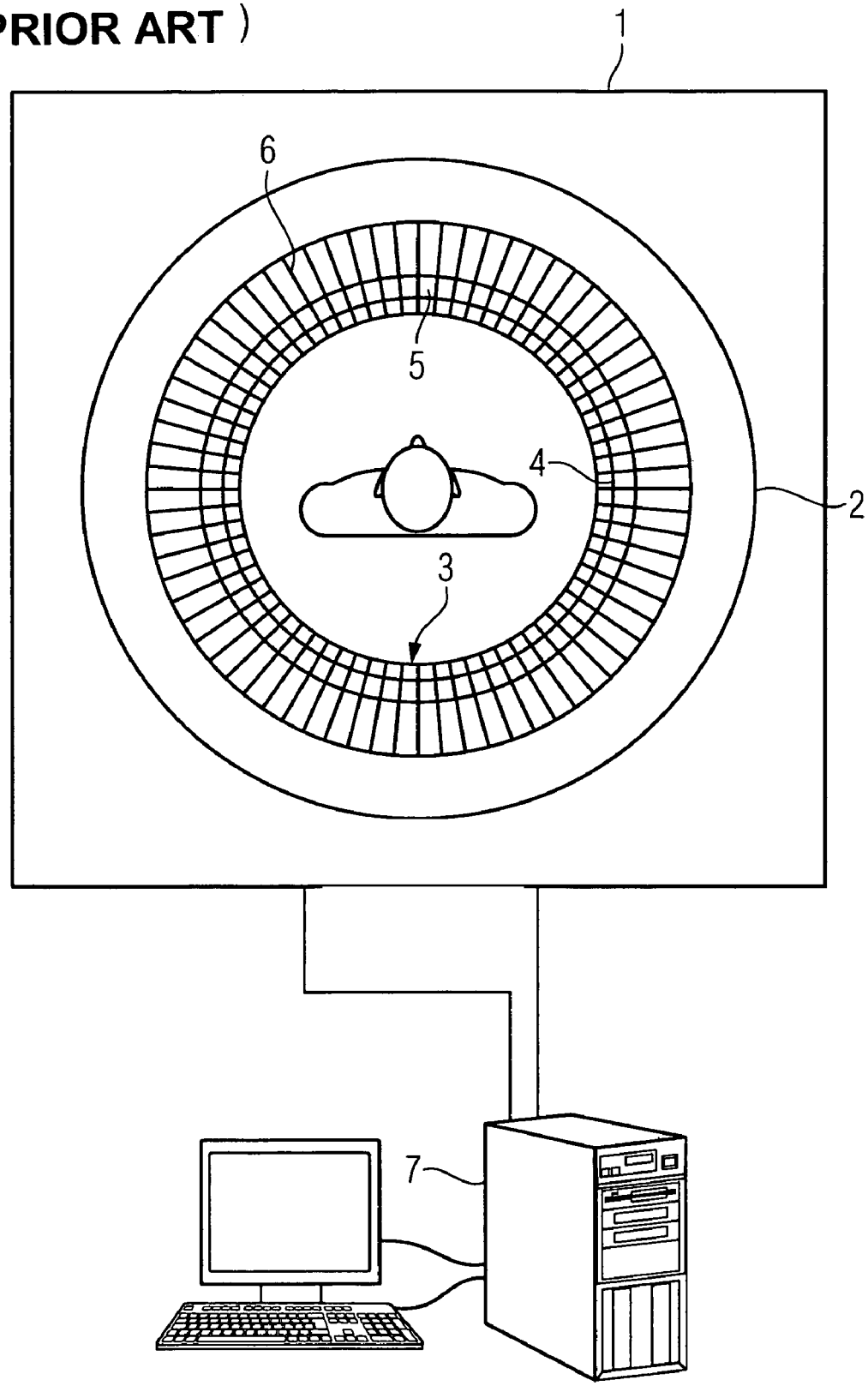
FIG. 1 a schematic diagram of a combined PET-MR unit.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the, " are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention can preferably be used on a combined PET-MR device. A combined device has the advantage that both MR and also PET data can be obtained egocentrically. This enables the examination volume within the region of interest to be defined precisely with the data of the first modality (PET) and this information to be used in the further modality (e.g. magnetic resonance device). Although a transmission of the volume information of the region of interest from an external PET to an MR device is possible, this results in an increased outlay for the registration of the data.

In general all data able to be defined with magnetic resonance or other imaging methods can be determined on the region of interest selected on the PET data set. For example instead of the spectroscopy data, firm data, diffusion data T1 or T2 weighted images or quantitative parameters can be obtained by means of magnetic resonance examinations in the region of interest. Likewise methods of computer tomography (e.g. perfusion measurement, multiple energy imaging) or x-rays can be used.

As an addition however it is also possible, by using a number of so-called tracers, to represent different biological characteristics in the PET data set and thus further optimize the region of interest and the volume defined thereby or to select a number of different examination volumes at once which are then analyzed in subsequent examinations.

Similarly the example embodiments of the invention can also be applied to hybrid modalities with non-egocentric examination volumes, such as for example known PET-CT systems.

FIG. 1 shows a known facility 1 for overlaid MR and PET image display. The facility 1 consists of a known MR tube 2. The MR tube 2 defines a longitudinal direction z, extending orthogonally in relation to the plane of the drawing depicted in FIG. 1.

As is shown in FIG. 1, a number of PET detection units 3 are arranged coaxially within the MRI tubes 2 in opposing pairs around the longitudinal direction z. The PET detection units 3 preferably consist of an APD photo diode array 5 with an upstream array of LSO crystals 4 and an electrical amplifier circuit (AMP) 6. The invention is however not restricted to the PET detection units 3 with the APD photo diode array 5 and the upstream array of LSO crystals 4, but other types of photo diodes, crystals and devices can likewise be used for detection.

The image processing for overlaid MR and PET image display is undertaken by a computer 7.

Along its longitudinal direction z the MR tube 2 defines a cylindrical first image field. The plurality of PET detection units 3 defines along the longitudinal direction z a cylindrical second image field. Inventively the second image field of the PET detection units 3 essentially matches the first image field of the MR tubes 2. This is implemented by a corresponding adaptation of the arrangement density of the PET detection units 3 along the longitudinal direction z.

Figure 2:
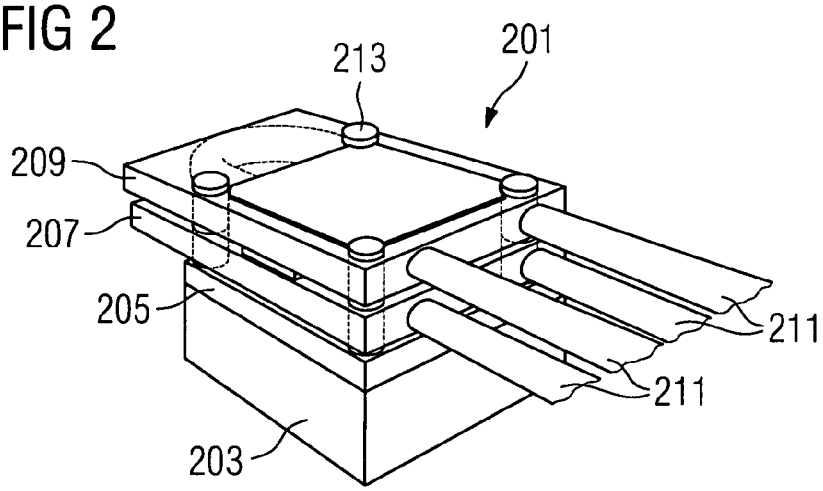
FIG. 2 a perspective schematic diagram of an example embodiment of the invention and FIG. 3 a schematic cross-sectional diagram of the example embodiment of the invention.

Shown in FIG. 2 is a schematic perspective diagram of a preferred embodiment of the invention. It comprises a detection unit 201 which in the lower area features an LSO crystal 203. Arranged above the LSO crystal 203 are an optical waveguide 205 and two cooling units 207 and 209. The coolant line 211 passes through each of the cooling units 207 and 209 at two points, enabling them to be cooled with coolant. The LSO crystals 203, the optical waveguides 205 and the two cooling units 207 and 209 are linked by retaining elements 213. Not shown in this Figure are a number of APDs and a number of electronic components of a signal processing unit arranged between the cooling units 207 and 209. This is shown in detail in FIG. 3.

Figure 3:
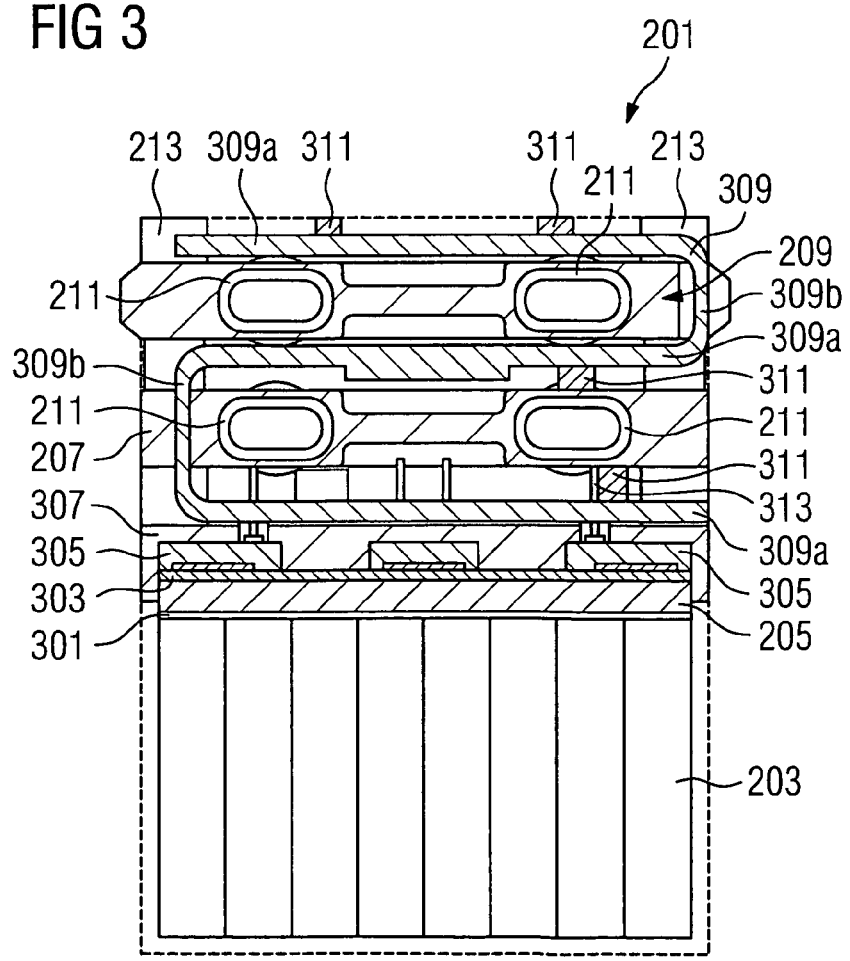

FIG. 3 shows a schematic cross sectional diagram through the detection unit 201. Introduced between the LSO crystal 203 and the optical waveguide 205 is a connecting layer 301. Attached to the optical waveguide 205 is an intermediate layer 303 above which a number of APDs 305 are arranged within a holder 307. The two cooling units 207 and 209 are in turn arranged above the holder 307. A cooling line 211 runs in two places each of the cooling units 207 and 209, through which the cooling units 207 and 209 can be supplied with cooling water. The cooling line 211 is embodied within the cooling units 207 and 209 such that coolant coming from the coolant source not shown here initially flows through the cooling unit 207. In the further route of the cooling line 211 this line carries coolant through the cooling unit 209. In this way both the cooling unit 207 and also the cooling unit 209 can be used for cooling down the APD 305 by means of a single cooling source.

Introduced between the cooling units 207 and 209, as well as the holder 307, is a circuit board 309. This has rigid sections 309a and flexible sections 309b and can thus be manufactured in one piece. The circuit board 309 is equipped with various electronic components 311. It also has electrical connections 313 to the APD 305. The components 311 located on the different sections 309a are able to be connected via conductor tracks via the flexible sections. The connection of the rigid and flexible sections 309a and 309b still enables the compact design shown to be implemented with a comparatively large circuit board surface.

The electronic 17 components 311 or the board 309 are in thermal contact with the cooling units 207 and 209 at a number of points. Consequently these are also cooled by the cooling units 207 and 209. Since a part of the circuit board 309 and some of the components 313 located on it lies between the cooling unit 207 and the holder 307 of the APD 305, there is no provision for a direct thermal contact between the APD 305 and the cooling unit 207 in this design. The thermal conductivity between the APD 305 via the holder 307, the circuit board 309 and the components 313 and the cooling unit 207 is sufficiently high however with the correct choice of the materials used in order to guarantee a good thermal coupling of the APD 305 to the cooling unit 207.

The Gamma quants created for PET events by scintillation are converted into light by the LSO crystal 203. The created light is forwarded via the optical waveguide 205 to the APD 305. These create pulses from the incident light stream which are passed on via the lines 313 to the circuit board 309 and its components 311. A provisional processing of received signals takes place on the circuit board 309. The amplification of the APD 305 is temperature-dependent, which would lead to measurement inaccuracies with insufficient cooling down. Thus a temperature stabilization in the range of a few degrees Celsius is to be realized here in order to guarantee a smooth operation of the detection unit 201. The cooling unit 207 in good thermal contact with the holder 307 of the APD 305, such that an efficient and easy-to-implement cooling of the APD 305 is provided. The self-heating of the APD 305 during operation can be compensated for in this way.

The compact layout of PET-MR systems means that in general there are a number of the detection devices 201 in the built-in state in the vicinity of various heat sources. In this case the gradient coil in particular plays a significant role. Its temperature fluctuates depending on the operating state between around 20 and 80° C. The incident heat on the outside of the APD 305 resulting from this has a significant effect on its operating temperature and thus on its amplification. The cooling unit 209 lying between the gradient coil and the APD 305 greatly reduces this incident heat, so that the operating behavior of the APD 305 is no longer subjected to any negative influences.

Basically the advantages of the example embodiments described can also be used in other circuit arrangements. For example the precise location of the circuit board 309 and its components 311 are not of any great significance. They could also be cooled by another cooling unit with greater effort. The compact layout however has advantages as have been described above.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A detection device, comprising:
   at least one detector unit embodied as a Positron Emission Tomography (PET) detector:
   a processing unit linked electrically with the at least one detector unit for processing electrical signals of the detector unit:
   a facility for cooling the detection device, the facility including,
      at least one first cooling unit in thermal contact with the detection device to remove heat arising during operation of the detection device; and
      at least one second cooling unit, arranged to discharge heat from an environment of the detection device through the at least one second cooling unit, wherein the processing unit includes at least one circuit board on which electronic components are arranged such that each of the components is in thermal contact with one of the at least one first cooling unit and the at least one second cooling unit and a number of circuit boards are provided with components which are arranged to alternate with the at least one first and at least one second cooling units.

2. The detection device as claimed in claim 1, wherein the at least one first and at least one second cooling units are arranged above the detection device as a stack.

3. The detection device as claimed in claim 2, wherein the at least one first cooling unit and the at least one second cooling unit each have at least one channel for the through flow of a coolant.

4. The detection device as claimed in claim 3, wherein the at least one channels of the first and the second cooling units are linked into a coolant circuit.

5. The detection device as claimed in claim 4, wherein the at least one first cooling unit and the at least one second cooling unit are arranged in the cooling circuit such that coolant flows through the at least one first cooling unit before flowing through the at least one second cooling unit.

6. The detection device as claimed in claim 1, wherein the at least one first cooling unit has a cooling surface through which a thermal contact to the detection device is able to be established.

7. The detection device as claimed in claim 6, wherein the at least one first and at least one second cooling units have further cooling surfaces, through which electronic components of the detection device are able to be brought into thermal contact with at least one of the at least one first and at least one second cooling units.

8. The detection device as claimed in claim 1, wherein the circuit boards lying above and below one of the cooling units, in each case being connected by flexible intermediate sections.

9. The detection device as claimed in claim 1, wherein the PET detector comprises at least one Avalanche Photo Diode (APD).

10. The detection device as claimed in claim 9, wherein the APD is arranged such that it is in thermal contact with the at least one first cooling unit.

* * * * *